United States Patent [19]

Immer et al.

[11] Patent Number: 5,767,239
[45] Date of Patent: Jun. 16, 1998

[54] PROCESS FOR PREPARING CARDIODILATIN FRAGMENTS; HIGHLY PURIFIED CARDIODILATIN FRAGMENTS AND INTERMEDIATE PRODUCTS FOR THE PREPARATION OF SAME

[75] Inventors: Hansueli Immer, Balsthal, Switzerland; Wolf-Georg Forssmann; Knut Adermann, both of Hanover, Germany; Christian Klessen, Lauterecken, Germany

[73] Assignee: Boehringer Mannheim GmbH, Mannheim, Germany

[21] Appl. No.: 737,927

[22] PCT Filed: May 30, 1995

[86] PCT No.: PCT/EP95/02050

§ 371 Date: Dec. 2, 1996

§ 102(e) Date: Dec. 2, 1996

[87] PCT Pub. No.: WO95/33769

PCT Pub. Date: Dec. 14, 1995

[30] Foreign Application Priority Data

Jun. 2, 1994 [DE] Germany .......................... 44 20 381.0
Apr. 10, 1995 [DE] Germany .......................... 195 13 784.1

[51] Int. Cl.⁶ .......................... A61K 38/10; A61K 38/12; A61K 38/16
[52] U.S. Cl. .......................... 530/339; 530/324; 530/325; 530/326; 530/327; 530/333; 530/334; 530/335
[58] Field of Search .......................... 530/339, 335, 530/334, 333, 324, 325, 326, 327

[56] References Cited

U.S. PATENT DOCUMENTS 5,449,751  9/1995  Forssmann et al. .......................... 530/324
5,665,861  9/1997  Forsemann et al. .......................... 530/334

Primary Examiner—David Saunders
Assistant Examiner—F. Pierre VanderVegt
Attorney, Agent, or Firm—Nikaido Marmelstein Murray & Oram LLP

[57] ABSTRACT

The invention relates to a process for the preparation of cardiodilatin fragments, to highly purified cardiodilatin fragments, and to appropriate intermediates for the preparation of said fragments. Furthermore, the invention relates to highly purified cardiodilatin fragments which are free of peptide impurities and exhibit a single migration peak in capillary electrophoresis, as well as to appropriate processes for the preparation of same.

8 Claims, 6 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:1:

```
Cys  Phe  Gly  Gly  Arg  Met  Asp  Arg  Ile  Gly  Ala  Gln  Ser  Gly  Leu  Gly
 1              5                        10                       15
Cys
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:2:

```
Leu  Arg  Ala  Leu  Leu  Thr  Ala  Pro  Arg  Ser  Leu  Arg  Arg  Ser  Ser
 1              5                        10                       15
```

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

Asn  Ser  Phe  Arg  Tyr
     1                      5

(2) INFORMATION FOR SEQ ID NO:4:

(i) SEQUENCE CHARACTERISTICS:
        (A) LENGTH: 32 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Thr  Ala  Pro  Arg  Ser  Leu  Arg  Arg  Ser  Ser  Cys  Phe  Gly  Gly  Arg  Met
     1                   5                         10                          15

Asp  Arg  Ile  Gly  Ala  Gln  Ser  Gly  Leu  Gly  Cys  Asn  Ser  Phe  Arg  Tyr
                    20                           25                         30

(2) INFORMATION FOR SEQ ID NO:5:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product="OTHER"
          / note= "hydroxy group is protected by Boc
          (t-butyloxycarbonyl)"

(xi) SEQUENCE DESCRIPTION: SEQ ID NO:5:

Thr  Ala  Pro  Arg
     1

PROCESS FOR PREPARING CARDIODILATIN FRAGMENTS; HIGHLY PURIFIED CARDIODILATIN FRAGMENTS AND INTERMEDIATE PRODUCTS FOR THE PREPARATION OF SAME

This application is a 371 of PCT/EP95/02050.

FIELD OF THE INVENTION

The invention relates to a process for the preparation of cardiodilatin fragments, to highly purified cardiodilatin fragments, and to appropriate intermediates for the preparation of said fragments.

BRIEF SUMMARY OF THE INVENTION

The present invention is directed to a process for the preparation of cardiodilatin fragments of formula I $$R^1\text{—ANP(105–121)—}R^2 \qquad (I)$$

having a chain length of 17–37 amino acids in total, wherein ANP(105–121) represents the amino acid sequence [SEQ ID NO. 1], R represents an amino acid chain of sequence ANEI (90–104) [SEQ ID NO. 2] or fragments thereof having a chain length of 0–15 amino acids, and $R^2$ represents an amino acid chain of sequence ANP (122–126) [SEQ ID NO. 3] or fragments thereof having a chain length of 0–5 amino acids, wherein synthesis is effected via condensation of at least three partial fragments, and condensation of the partial fragments to give the cardiodilatin fragments of formula I is carried out between the amino acid positions $Gly^{108}$ and $Arg^{109}$ and the amino acid positions $Gly^{120}$ and $CyS^{121}$.

Cardiodilatin is a peptide of the class of natriuretic peptides. These peptides play an important role in regulating the balance of salts and water in the body. The prototype of natriuretic hormones is cardiodilatin, also referred to in literature as atrial natriuretic peptide (CDD/ANP). The isolation of cardiodilatin and the preparation of biologically active fragments of cardiodilatin are known from U.S. Pat. No. 4,751,284 (cf., W. G. Forssmann et al., Klin. Wochenschr. 1986, 64 (Suppl. VI), 4–12). A review on isolation and characterization of cardiodilatin and fragments thereof, as well as their physiological properties has been published in Eur. J. Clin. Invest. 1986, 16; 439–451 (W. G. Forssmann). From EP 0,349,545, a specific cardiodilatin fragment having a chain length of 32 amino acids is known. Meanwhile, this fragment is also referred to in literature as urodilatin (INN: ularitide). Furthermore, U.S. Pat. No. 5,354,900 (Suntory) describes a biologically active fragment having a chain length of 28 amino acids, known as α-hANP. Further biologically active cardiodilatin fragments or derivatives thereof have been described in EP 0,180,615. Therein, in particular, cardiodilatin fragments are described which begin with the amino acid position $Arg^{102}$ at the N-terminus and end with the amino acid position $Arg^{125}$ or $Arg^{126}$ at the C-terminus. Instead of the designation cardiodilatin, the literature frequently uses the designation "atrial natriuretic peptide" (ANP). In the numbering of the sequences of the cardiodilatin amino acids used in the following, reference is made to the nomenclature used for the ANF/CDD (1–126) peptide (=ANP) in EP 0,349,545.

A common structural feature of all hitherto known biologically active cardiodilatin fragments is the formation of a disulfide bridge between the amino acids $Cys^{105}$ and $Cys^{121}$, resulting in a stable ring of 17 amino acids. It is believed that the formation of this ring is substantially responsible for the biological activity of the cardiodilatin derivatives. At position $Cys^{105}$, the cardiodilatin fragments are substituted by an amino acid chain $R^1$ having a chain length of 0–15 amino acids, and at position $Cys^{121}$ by a chain $R^2$ having a chain length of 0–5 amino acids. In the [SEQ ID NO. 1], the central region ANP(105–121) is presented in linearized form.

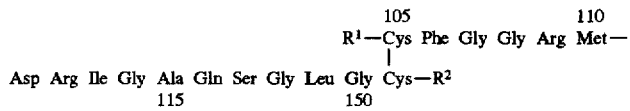

The cardiodilatin fragment ANP(95–126), with the INN designation ularitide, is a particularly stable and biologically active human peptide, having diuretic activity and a relaxing effect on the smooth vascular muscles, which is formed of 32 amino acids and has the following sequence, wherein both the cysteine amino acids at positions 11, and 27 in the peptide are forming a disulfide bridge (SEQ ID NO: 4):

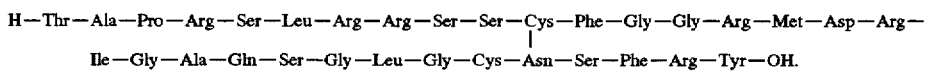

Urodilatin is found in human urine. EP 0,349,545 describes a process for recovering urodilatin from urine using alginic acid, wherein the peptides adsorbed to alginic acid are eluted, the eluate is fractionated according to conventional purification methods, and the active fraction is recovered using a test based on the examination of the relaxing effect of urodilatin on the smooth muscles.

Furthermore, EP 0,349,545 describes a stepwise chemical synthesis of urodilatin using the Merrifield process (J. Am. Chem. Soc. 1963, 85; 2149–2156), at a solid phase according to the ABI standard program following the Boc strategy. In addition, this patent specification describes the preparation of urodilatin from the partial fragment ANP(99–126). This fragment is bound to a solid phase, and is reacted with a second partial fragment, the tetrapeptide (SEQ ID NO. 5) Boc-Thr(But)-Ala-Pro-Arg(Tos). The peptide ANP(95–126) obtained from the condensation is removed from the support, subjected to cyclization after removal of the protecting groups and subsequently, is processed and purified in a per se known manner.

Similarly, EP 0,180,615 describes the chemical synthesis using a solid support, wherein formation of the cardiodilatin fragments described therein is effected successively, starting from the C-terminus in direction of the N-terminus. Here, condensation via partial fragments is not described.

However, the cardiodilatin fragments prepared according to the procedures described in literature did not have the purity necessary for clinical studies and for the authorization as medicinal product because, due to the synthesis, peptide impurities had been introduced into the final product which could not be removed even by subsequent purification processes. Due to their immunogenic properties, the impurities may give rise to undesirable side-effects when administered to the patient, so that therapeutic application involved risk. Moreover, the synthesis could be accomplished at only a small scale under reasonable technical input and was not economically suitable for a larger production scale. Furthermore, another drawback of known processes for synthesis was the existing potential risk of racemization due to which the urodilatin was obtained with lower purity, lower biological activity and in insufficient yield. Racemization of the product which frequently occurs with existing syntheses often resulted in insufficient optical purity of the final product, and these impurities frequently cannot be removed or only with exceedingly high technical input.

Thus, it is an object of the invention to develop an improved process for the chemical synthesis of cardiodilatin fragments which does not involve the above-mentioned drawbacks.

The object of the invention is attained by performing the synthesis of cardiodilatin fragments on the basis of the Merrifield process using a specific selection of peptide fragments.

Surprisingly, the course of synthesis has been found to be optimal when the cardiodilatin fragments are formed using three partial fragments, with the condensation of the partial fragments to give the cardiodilatin fragment of formula I being performed in such fashion that the formation is effected via condensation of partial fragments and bond formation between the amino acid positions $Gly^{108}$ and $Arg^{109}$ and the amino acid positions $Gly^{120}$ and $CyEy^{121}$. This process is advantageous in that the cardiodilatin fragments of formula I can be obtained in higher yields and in higher purity as compared to the synthetic processes known from prior art.

DETAILED DESCRIPTION OF THE INVENTION

Figure 1:
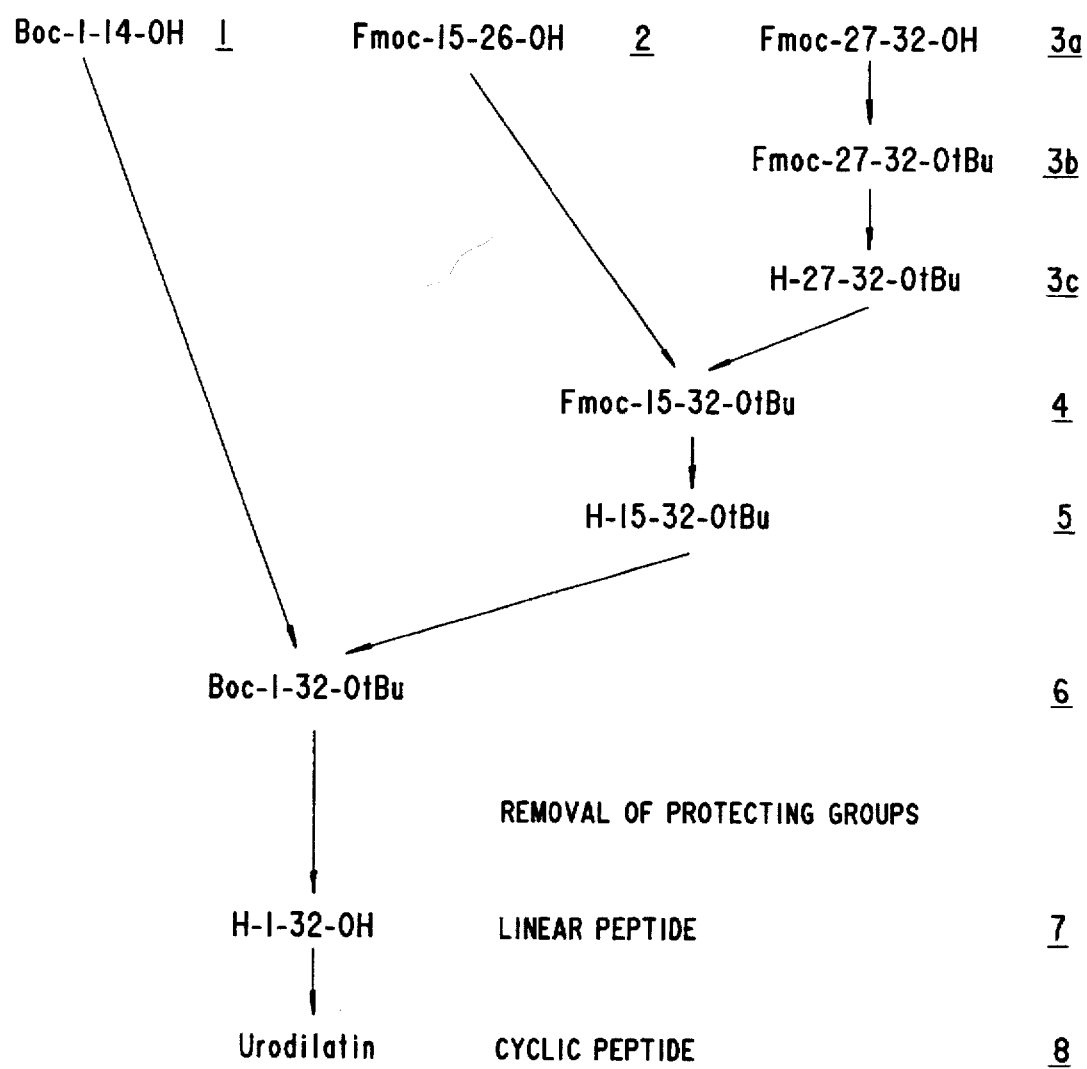
FIG. 1 is a flow diagram illustrating the principle of synthesis using the condensation method, depicting urodilatin as an example.

The synthesis of the cardiodilatin fragments of formula I is effected in such way that initially, the three partial fragments having the sequences $R^1$-ANP(105–108), ANP (109–120) and ANP(121)-$R^2$ are prepared according to the Merrifield process. Then, preferably, condensation of the three partial fragments to give the cardiodilatin fragment of formula I is effected in two partial steps, whereby in a first step, condensation between the amino acid positions $Gly^{120}$ and $Cys^{121}$ of the partial fragments ANP(109–120) and $Cys^{121}$-$R^2$ is effected, with the intermediate fragment ANP (109–121)-$R^2$ being formed. Then, in a subsequent second step, condensation of the thus obtained fragment ANP (109–121)-$R^2$ with the third partial fragment $R^1$-ANP (105–108) is effected, forming the desired cardiodilatin fragment of formula I. Using the process according to the invention, the yield of cardiodilatin fragments is between 15 and 20%, based on the amount of each cardiodilatin partial fragment used as starting material.

The three partial fragments having the sequences $R^1$-ANP (105–108), ANP(109–120) and ANP(121)-$R^2$ are prepared according to the Merrifield process, wherein the amino acids with functional groups (hydroxy, carboxy, amino, or mercapto groups) present in the sequence are substituted by appropriate protecting groups. For example, as suitable protecting groups the following groups are possible:

protecting groups for hydroxy groups: Boc (t-butyloxycarbonyl), tBu (t-butyl ether);

protecting groups for amino functions: Fmoc (9-fluorenylmethoxycarbonyl), Pbf (2,2,4,6,7-pentamethyldihydrobenzofuran-5-sulfonyl), Pmc (2,2,5,7,8-pentamelhyl-chroman-6-sulfonyl), Trt (trityl);

protecting groups for carboxy groups: OtBu (t-b)utyl ester);

protecting groups for mercapto groups: Acm (acetamidomethyl) or Trt.

Here, the following protecting groups are preferred for the following amino acids: tBu for the amino acids Thr, Asn, Tyr or Ser; Pbf or Pmc for the amino acid Arg; Acm for the amino acid Cys; OtBu for the amino acid Asp; Trt: for the amino acids Gln, Asn or Cys.

Using the Fmoc strategy (B. Riniker et al., Tetrahedron 1993, 49; 9307–9320), the protected partial fragments ANP (109–120), $R^1$-ANP(105–108) and ANP(121)-$R^2$ are formed on a solid support material. All the materials generally used in the Merrifield synthesis may serve as solid support materials. Preferred as support material is polystyrene functionalized as aminomethyl or benzhydrylamino compound. The superacid-sensitive bonding of the peptide fragments to the resin by means of the 4-(4-hydroxymethyl3-methoxyphenoxy)butyric acid linker allows their removal without impeding the side-chain protection. The fragments are purified by digestion with various solvents. Thus, the three starting fragments ANP(109–120), $R^1$-ANP(105–108) and ANP(121)-$R^2$ are obtained with a C-terminal free carboxyl group and in good purity. When forming the peptides on the support resin, the yield in every single step of addition of one amino acid is nearly quantitative and is about 97–99%.

Figure 2:
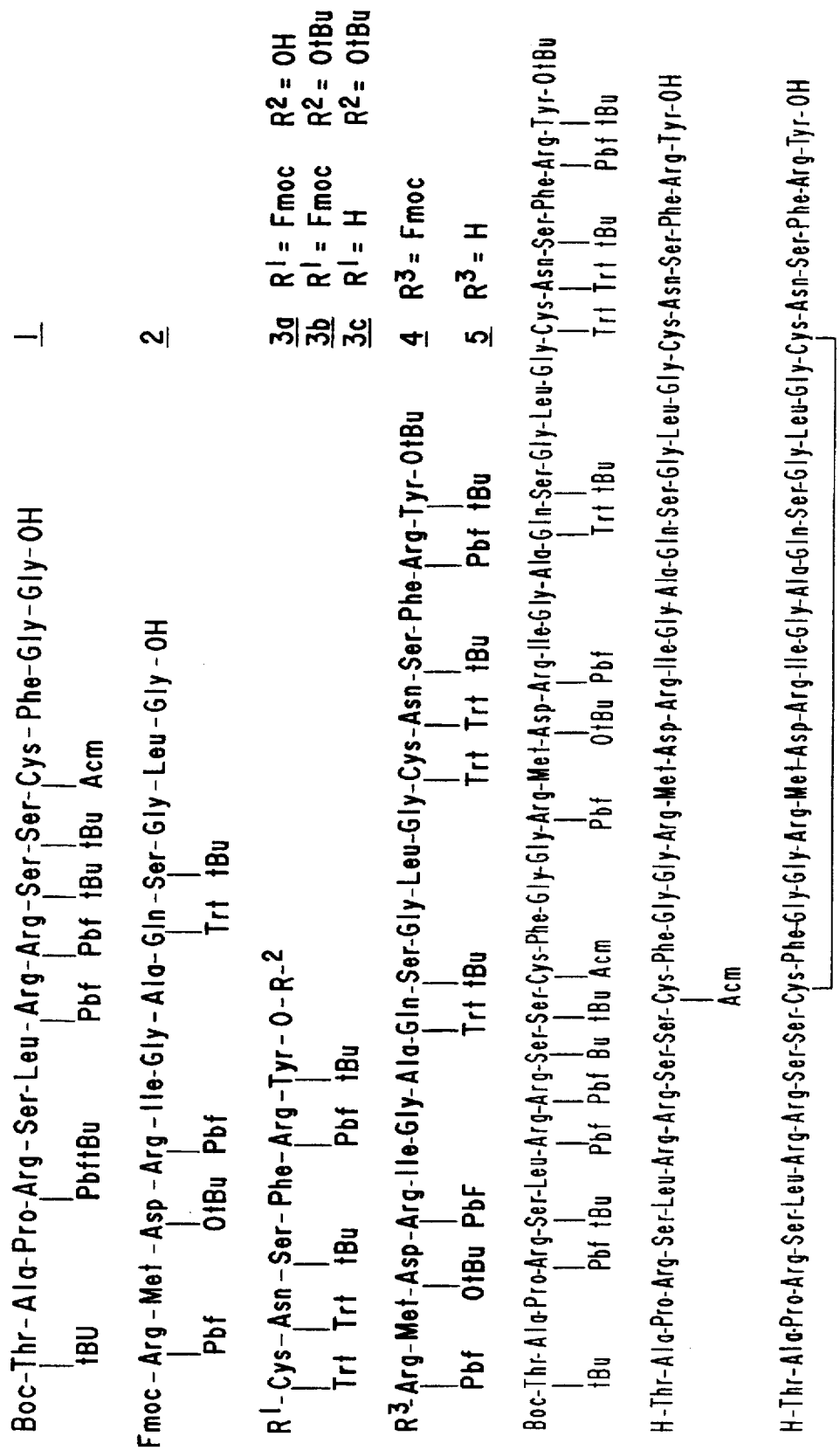
FIG. 2 is a representation of the fragments $R_1$, (SEQ ID NO:2); ANP (105–121), SEQ ID NO: 1); and $R_2$, (SEQ ID NO:3) and the products of their condensation.

The flow diagram in FIG. 1 illustrates the principle of synthesis, with urodilatin ANP(95–126) as an example. Here, condensation of the fragment Boc-1-14-OH. (1) [this nomenclature corresponds to the general designation of fragment $R^1$-ANP(105–108), wherein $R^1$=ANP(95–104)] with the fragment H-15-32-OtBu (5) [corresponding to an ANEP nomenclature of ANP(109–121)-$R^2$, wherein $R^2$=ANP(122–126)] is effected. This fragment (5) is synthesized from the fragments Fmoc-15-26-OH (2) [corresponding to an ANP nomenclature of ANP(109–120)]

and H-27-32-OtBu (3c) [corresponding to an ANP nomenclature of ANP(121)-R²]. FIG. 2 represents the fragments synthesized and modified with protecting groups.

In the next step, the carboxyl group of fragment (3a) is converted to the t-butyl ester (3b) (cf., Riniker et al., 22nd Europ. Peptide Symposium Interlaken, September 1992 (L7)). Subsequent removal of the Fmoc group from fragment (3b) leads to the product (3c). This is fused with fragment (2), resulting in fragment (4). Removal of the Fmoc protecting group and condensation of the obtained fragment (5) with fragment (1) leads to the fully protected urodilatin (6). Removal of the protecting groups by treatment with trifluoroacetic acid and 1,3-propanedithiol as a scavenger provides the linear peptide (7) which is cyclized to crude urodilatin (8) by oxidation with iodine solution. This is desalted, purified and may be lyophilized subsequently. The synthesis of other cardiodilatin fragments is conducted in an analogous fashion.

The synthesis according to the invention, involving the described partial fragments ANP(109–120), R¹-ANP(105–108) and ANP(121)-R² may be applied to all the cardiodilatin fragments of formula I. In particular, cardiodilatin fragments are possible, wherein R¹ has a chain length of 0–15 amino acids of the sequence ANP(90–104) or fragments thereof. Preferred for R¹ are chain lengths of 1–15 or 3–10 amino acids, particularly the sequences ANP(95–104), ANP(99–104) and ANP(102–104). In particular, the group R² represents a chain length of 1–5 amino acids of the sequence ANP(122–126) or fragments thereof. Preferably, however, the sequences ANP(122–126) and ANP(122–125) are possible for R².

Preferably, the cardiodilatin fragments ANP(95–126), ANP(99–126) and ANP(102–126) may be prepared according fragments prepared by means of the process of the invention, to the process of the invention. The cardiodilantin as well as the partial fragments required for condensation have high optical purity in the range of about 96–99.9%, particularly about 98–99%.

Similarly, the synthesis is suitable for all the other derivatives of cardiodilatin fragments wherein one or more amino acids in the sequence of human ANP are replaced by other amino acids. In this meaning, replacement of amino acids includes corresponding substitutions, deletions or insertions of amino acids. For example, single or multiple amino acids may be replaced by the corresponding D-amino acids (cf., EP 0,180,615). Likewise, peptides of similar structure and with a corresponding cyclic basic structure of 15–20 amino acids may be prepared in this way. Examples of such peptides are BNP (brain natriuretic peptide) or CNP (C-type natriuretic peptide). The structures of these peptides are described in J. Hypertension 1994, 12; 329–336 (N. C. Davidson and A. D. Struthers).

Likewise, the present invention is directed to novel partial fragments of ANP which are utilized for the preparation of cardiodilatin fragments of formula I according to the process of the invention.

More specifically, corresponding peptide fragments are those of the type R¹-ANP(105–108), wherein R¹ reapresents an amino acid chain of sequence ANP(90–104) or fragments thereof having a chain length of 0–15 amino acids, as well as their derivatives modified by protecting groups. Here, in particular, R¹ has the above-mentioned meanings. Another novel peptide fragment is the fragment having the amino acid sequence ANP(109–120), as well as its derivatives modified by protecting groups, which is employed as a starting material in the condensation with the partial fragment ANP(121)-R². Likewise, the corresponding ANP(121)-R² type peptide fragments represent a novelty and a subject matter of the invention, wherein R² represents an amino acid chain of sequence ANP(122–126) or fragments thereof having a chain length of 0–5 amino acids, as well as their derivatives modified by protecting groups. In particular, R² has the previously mentioned meaning. In addition, the invention is directed to the intermediate ANP(109–121)-R² which is formed from the condensation reaction of the partial fragments ANP(109–120) and ANP(121)-R² effected in the first reaction step.

Furthermore, the present invention relates to a process for preparing high-purity cardiodilatin fragments of formula I. Conventional synthetic processes and subsequent purification procedures on cardiodilatin fragments suffered from the drawback that in many cases a peptide purity in a range of merely 97–98% could be achieved.

EP 0,349,545 describes a purity level of about: 98% in the case of urodilatin; therein, the amount of urodilatin prepared was merely on a smaller laboratory scale in the range of a few milligrams. The purification procedure described in Example 5 therein is based on a chromatography on a LH column (eluant: 1% AcOH, 1% TFEtOH) and subsequent chromatography on a TSK column (Fractogel TSK-HW 40), wherein an aqueous solution of 10% ACOH and 1% TFEtOH was used as the eluant. In a final purification step, purification using preparative HPLC is effected, without any further indications on the eluant being made. Within the scope of later experiments on the preparation of larger amounts of urodilatin in the range of a few grams for performing clinical tests, it was determined, however, that in spite of multiple purification steps, the synthesized material could not be purified beyond a purity level of more than 98%.

A comparable situation resulted in the case of cardiodilatin fragments described in EP 0,180,615. Therein, for example, the purification for fragment ANP(102–126)—in Example III.A.3 referred to as hANVP(127–151) by chloromatography on a type G25F Sephadex column is described, where 0.5 M AcOH was used as the eluant. In a subsequent purification step by means of ion exchange chromatography on CM Sepharose or CM Cellulose using a solvent gradient of 0.01M NH₄OAc/300 mM NH₄OAc at pH 4.5, the peptide is obtained in a purity of about 97%. Likewise, this purity achieved is not satisfactory for the requirements in drug manufacturing.

Surprisingly, it has been found that high-purity cardiodilatin fragments of formula I can be prepared if the crude product is purified using a reversed-phase HPLC column, and the cardiodilatin fragment is eluted using a buffer system containing triethylammonium phosphate (TEAP) and acetonitrile in aqueous solution. Here, preferably, the pH value of the elution buffer is adjusted to a value of 2–5, more specifically, of 2–3. Preferably, a type C₁₈ column, for example, Biotage module type filled with YMC C₁₈ is used as the reversed-phase HPLC column. This column is equilibrated with triethylammonium phosphate buffer prior to loading the cardiodilatin fragments to be purified. For example, a solution of 10–200 mM TEAP, preferably 50 mM TEAP, is employed as a suitable buffer solution. The amount of buffer for column equilibration depends on the column size and this, in turn, on the amount of peptide to be purified. According to experience, a column volume of 75×300 mm (diameter×length) is required to purify an amount of peptide of 3–8 g of crude peptide. In this case, about 300 ml of a 50 mM TEAP buffer solution is required for equilibration. Subsequently, a solution of the concentrated crude product of cardiodilatin fragment is applied. As a solvent, for example, 10% acetic acid is suitable. Thereafter, the peptide is eluted in a continuous gradient by continuous charging of eluant (mixture of an aqueous solution of 10–200 mM TEAP and acetonitrile at a volume ratio of 2:3; pH 2–5). Elution of peptide is particularly advantageous if a continuous gradient of eluant is applied, where 22–28% of solvent gradient is used for a period of 90 minutes, followed by 28% of solvent gradient for 10 minutes and, eventually, 28–40% of gradient for 20 minutes. Preferably, the flow rate is 100–200 ml/min, more specifically, about 140 ml/min. In the meaning of the purification process according to the invention, a buffer mixture of triethylammonium phosphate in water and acetonitrile at a mixing ratio of from 1:3 to 2:1 (v/v), more specifically of about 2:3 (v/v) is used as elution buffer. The pH value of the buffer solution is 2–5, preferably 2–3, and more specifically about 2.25. TEAP may be used at a concentration of 10–200 mM, preferably 20–100 mM, and more specifically, of about 50 mM. According to the invention, optimum separation is achieved in the reversed-phase HPLC by equilibrating the column using 50 mM TEAP, pH 2.25, and eluting the peptide with a buffer consisting of 50 mM TEAP, pH 2.25, and acetonitrile at a ratio of 2:3.

Figure 5:
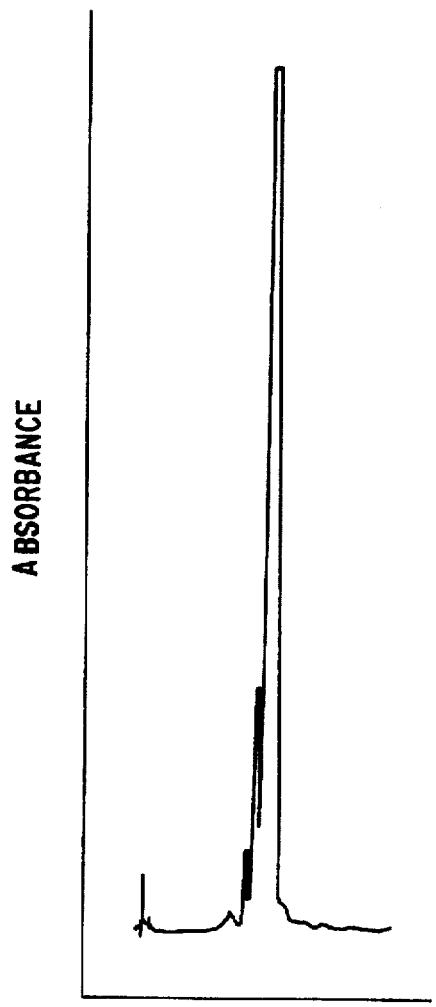
FIG. 5 illustrates the purification of urodilatin and the separation of impurities by high-performance liquid chromatography according to FIG. 6 illustrates the inability to separate impurites from urodilatin according to conventional purification methods using trifluoroacetic acid.
Figure 6:
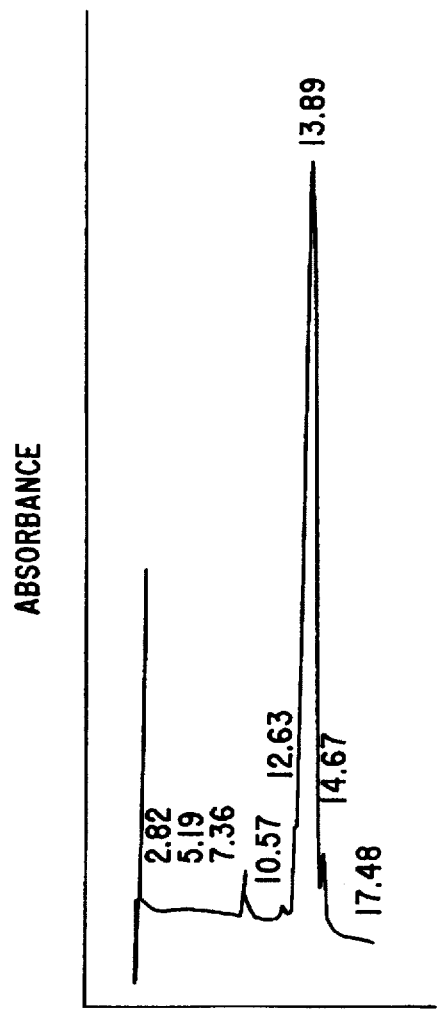

Conventional purification procedures using aqueous 0.1% trifluoroacetic acid (TFA), for example, are not capable of further separating the polar impurities contained, in the crude products, as are revealed in FIG. 5 in the example of urodilatin (FIG. 6). In contrast, in the case of the eluants used according to the invention, there is significant separation of both impurities (see FIG. 5). Furthermore, use of the eluant according to the invention is advantageous in that the base line in the HPLC chromatogram takes an absolutely steady course, while in the case of TFA, a strong drift can be observed. In addition, use of TFA suffers from the drawback that a higher back pressure builds up on the HPLC column, which is not the case for the eluant according to the invention.

Figure 3:
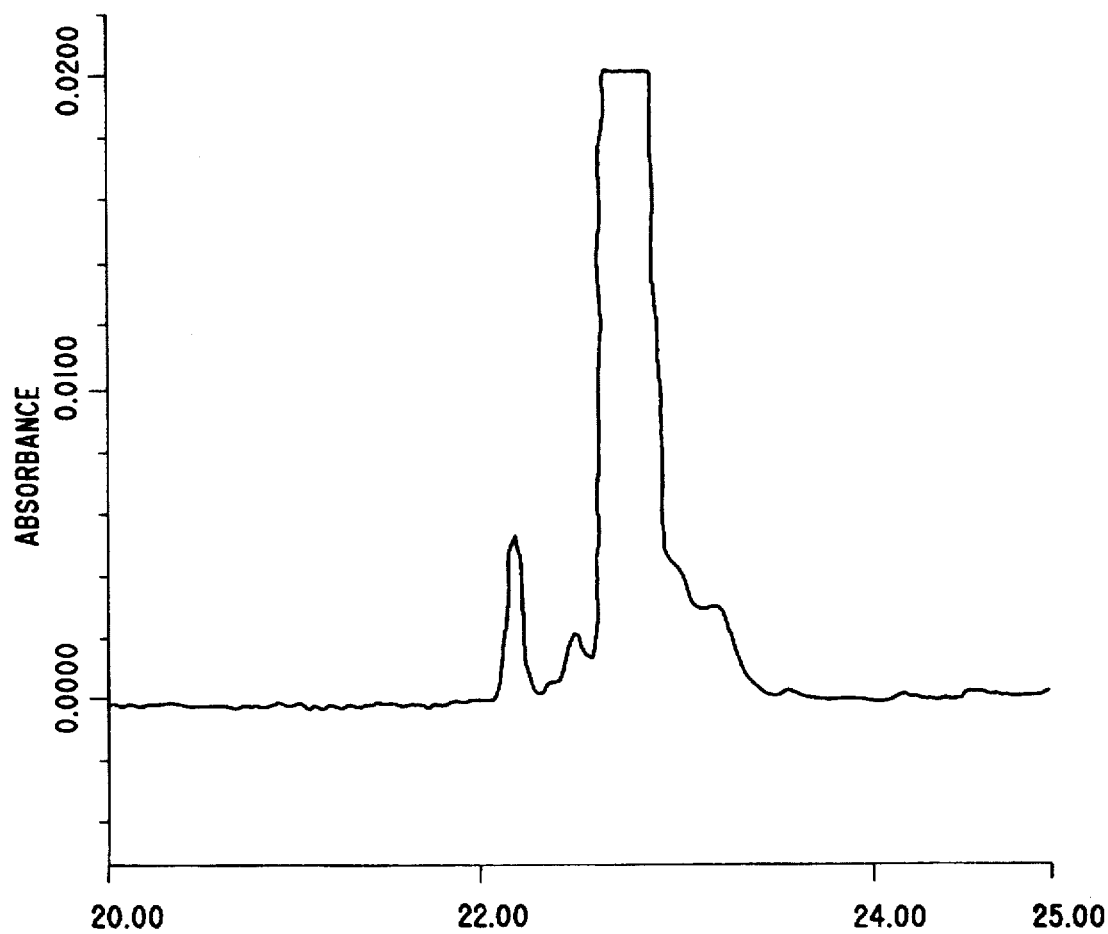
FIG. 3 illustrates the CE chromatogram of a urodilatin production batch produced according to the methods of the prior art.
Figure 4:
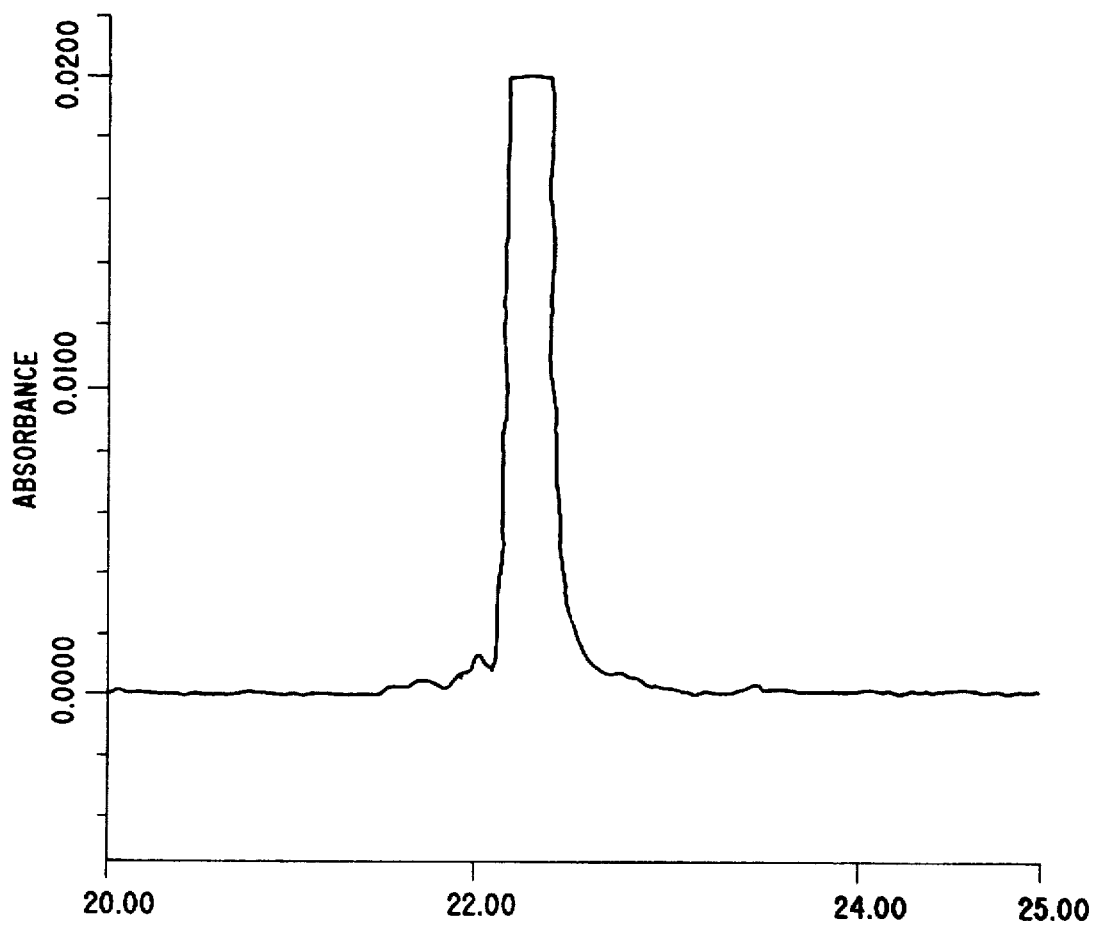
FIG. 4 illustrates the CE chromatogram of a urodilatin production batch produced according to the method of the present invention.

Using the process according to the invention, high-purity cardiodilatin fragments of formula I are obtained in a purity of at least 99% and preferably, of up to 99.9%. Optionally, the cardiodilatin fragments may subsequently be converted to their physiologically acceptable salts, such as the acetate or citrate salts. The cardiodilatin fragments obtained are substantially free of peptide impurities so that not only the reversed-phase HPLC exhibits a single peak but also the much more sensitive method of capillary electrophoresis (CE) provides a single migration peak. In the case of urodilatin, the latter shows a mass of 3505.9±1 in the MS analysis, without byproducts being detected. It turned out that the use of capillary electrophoresis allows an excellent demonstration of the differences between cardiodilatin fragments obtained according to prior art and the cardiodilatin fragments according to the invention. FIG. 3 illustrates the CE chromatogram of a urodilatin production batch produced according to prior art. Herein, it can be clearly seen that the product still contains impurities. In contrast, FIG. 4 represents the CE chromatogram of a urodilatin production batch produced according to the process of the invention and purified correspondingly. It is clearly obvious that the product is substantially free of other peptide impurities and exhibits a single migration peak in the capillary electrophoresis.

Therefore, the invention is directed to high-purity cardiodilatin fragments of formula I which are remarkable in that they do not contain substantial peptide impurities detectable by capillary electrophoresis and MS analysis, and that the purity analysis using capillary electrophoresis exhibits a single migration peak.

Similarly, the purification procedure according to the invention is also suitable for the preparation of analogous high-purity peptide compounds such as, e.g., BNP (brain natriuretic peptide), CNP (C-type natriuretic peptide) or derivatives thereof. The cyclic structure of ANP is based on the oxidation of two cysteine residues within the amino acid sequence, forming a cyclic ring of 17 amino acids. Other peptides which also form the characteristic cyclic structure of 15–20 amino acids, particularly 17 amino acids, such as, e.g., BNP or CNP, may be converted to the high-purity forms in the same fashion using the purification procedure according to the invention.

In the following embodiments, the invention will be illustrated using the selected representative cardiodilalin fragments ANP(95–126), ANP(99–126) and ANP(102–126).

Example 1

General Procedures of Solid-Phase Synthesis According to the Merrifield Process a) Solid-Phase synthesis on a support resin Starting from the C-terminus of the peptide to be synthesized, the first amino acid (AA) protected by the Fmoc group at the N-terminal end, is bound to the support resin (Fmoc-AA-OHMPB-support resin). With a standard batch of 6.66 mmoles, the Fmoc protecting group is subsequently removed by adding 100 ml of a solvent mixture of piperidine and N-methylpyrrolidine (1:4 v/v). Then, the resin suspension is stirred for 10 minutes, subsequently filtrated, and again, 100 ml of the piperidine and NMP solvent mixture is added. Then, the suspension is stirred for 10 minutes, filtrated and subsequently washed with NMP an isopropanol, and completeness of the reaction is checked using the Kaiser test.

Thereafter, the next amino acid is coupled to the resin. Initially, 20 mmoles of a 0.5M solution of diisopropylethanylamine (DIPEA) in NMP is added to the resin, then 2.5 mmoles of a 0.5M solution of 1-hydroxybenzotriazole (OHBT) in NMP, followed by 10 mmoles of the amino acid to be coupled in 25 ml of NMP. Thereafter, 11 mmoles of a 0.25M solution of TBTU (2-(1H-benzotriazol-1-yl)-1,1,3,3-tetramethyluronium tetrafluoroborate) in NMP is added and stirred for 10 minutes. Completeness of the reaction is checked using the Kaiser test. Subsequently, the resin is filtrated and washed with NMP.

This process is continued in the same way, until the peptide chain of desired chain length of amino acids is built up on the resin. When synthesis is complete, the resin is dried to constant weight at 40° C.

b) Removal of the protected peptides from the support resin

Each of 10 suction flasks is charged with 75 ml of methanol and 3 ml of pyridine. 50 g of the support resin prepared according to step a) is stirred 10 times with 250 ml of 1% TFA in dry methylene chloride for one minute on the suction funnel, and is filtrated directly into the respective suction flask. These 10 filtrates are checked using thin layer chromatography. Fractions containing product are combined and evaporated to dryness. The residue is triturated with deionized water, and the crystalline residue is filtrated off and dried.

Example 2

Preparation of Fragment ANP(109–120)

Following the general procedures of Example 1, and starting from 273 g of Fmoc-Gly-OHMPB-support resin (corresponding to 130 mmoles), 170.3 g of the fully protected cardiodilatin fragment ANP(109–120) is obtained.

Example 3

Preparation of Fragment ANP(121–126)

Following the general procedures of Example 1, and starting from 264 g of Fmoc-Tyr-OHMPB-support resin (corresponding to 115 mmoles), 150.7 g of the fully protected cardiodilatin fragment ANP(121–126) is obtained. Here, the N-terminal end of the fragment is protected by the Fmoc group.

Subsequently, the terminal hydroxy group at the C-terminal end of the fragment is converted to the OtBu protecting group. For esterification, 149 g of the fully protected fragment is dissolved in 500 ml of trifluoroethanol and 4.1 l of chloroform. This is followed by addition of 141 ml of TBTA (t-butyl-2,2,2-trichloroacetimidate), and the solution is heated at reflux for one hour. After the reaction is completed, the solution is concentrated to give a crystalline-oily residue. 6.8 l of diisopropyl ether is added, and the suspension is stirred at room temperature for 14 hours. The product is filtrated off and dried to constant weight. 136.7 g of fragment 3b indicated in FIG. 2 is obtained.

Subsequently, the Fmoc protecting group at IFhe N-terminal end of the fragment is removed, and conversion to fragment 3c indicated in FIG. 2 is effected. To this end, a solution of fragment 3b (135.7 g) in 1.8 l of DMF and 74 ml of diethylamine is stirred at room temperature for 3 hours. The solution is evaporated to complete dryness in a vacuum. The residue is digested with 1.4 l of deionized water and filtrated off. The wet product is taken up in 3 l of MTBE (methyl t-butyl ether). The solution is extracted with a saturated NaCl solution (2×100 ml), and the organic phase is dried with sodium sulfate. The solution is concentrated to a volume of 500 ml. Following acddition of 1.5 l of isopropyl ether, stirring for two hours is effected. The product is filtrated and dried. The yield, is 104.6 g of fragment 3c indicated in FIG. 2.

Example 4

Preparation of Fragment ANP(121–125)

In an analogous manner as described in Example 3, starting from 264 g of Fmoc-Arg(Pbf)-OHMPB-support resin and following the procedure described, 115.1 g of cardiodilatin fragment ANP(121–125) is obtained.

Example 5

Preparation of Fragment ANP(95–108)

Following the general procedures of Example 1, and starting from 210 g of Fmoc-Gly-OHMPB-support resin, 151.5 g of the fully protected cardiodilatin fragment ANP (95–108) is obtained.

Example 6

Preparation of Fragment ANP(99–108)

Following the general procedures of Example 1, and starting from 190 g of Fmoc-Gly-OHMPB-support resin, 145.1 g of the fully protected cardiodilatin fragment ANP (99–108) is obtained.

Example 7

Preparation of Fragment ANP(102–108)

Following the general procedures of Example 1, and starting from 220 g of Fmoc-Gly-OHMPB-support resin, 165.3 g of the fully protected cardiodilatin fragment ANP (102–108) is obtained.

Example 8

Condensation of the Partial Fragments to the Intermediate Product

The fragment ANP(109–120) is converted to the intermediate ANP(109–121)-$R^2$ by condensation with the C-terminal fragment ANP(121)-$R^2$ according to the following general process:

The fragment ANP(109–120), the amino terminus of which is protected by the Fmoc group, is dissolved in N-methylpyrrolidone. Subsequently, TBTU (2-(1H-benzotriazol-1-yl)-1,1,3,3-tetramethyluronium tetrafluoroborates), 1-hydroxybenzotriazole and diisopropylethylamine are added to the solution at room temperature with stirring. Thereafter, the fragment ANP(121)-$R^2$ provided with an appropriate protecting group at the C-terminal end and dissolved in N-methylpyrrolidone is added to the solution. In the following, the reaction is monitored by thin layer chromatography. After about 2 hours, the reaction is complete. Then, the reaction mixture is dripped onto diisopropyl ether with stirring and subsequently stirred for about 30 minutes. The precipitate is filtrated on a porcelain suction funnel over hard filter and washed twice with diisopropyl ether. Thereafter, the residue is suspended in acetonitrile and digested at room temperature with stirring. Subsequently, the product is filtrated on a porcelain suction funnel, rewashed with acetonitrile and dried to constant weight in a vacuum chamber at 40° C. The thus obtained crude product represents the cardiodilatin fragment Fmoc-ANP(109–121)-$R^2$ protected at the amino terminus by the Fmoc protecting group. Thereafter, the Fmoc group is removed according to known procedures to obtain the intermediate product H-ANP(109–121)-$R^2$.

Example 9

Condensation of Fragments ANP(109–120) with ANP(121–126) to ANP(109–126)

Following the general procedure described in Example 8, 21.6 g of Fmoc-ANP(109–120) is dissolved in 650 ml of N-methylpyrrolidone. Subsequently, 3.2 g of TBTU (2-(1H-benzotriazol-1-yl)-1,1,3,3-tetramethyluronium tetrafluoroborate), 1.5 g of 1-hydroxybenzotriazole and 3.5 ml of diisopropylethylamine are added to the solution at room temperature with stirring. Thereafter, a solution of H-ANP(121–126)-OtBu, dissolved in 150 ml of N-methylpyrrolidone, is added. In the following, the reaction is monitored by thin layer chromatography. After about 2 hours, the reaction is complete. Then, the reaction mixture is dripped onto 4 l of diisopropyl ether with stirring and subsequently stirred for about 30 minutes. The precipitate is filtrated on a porcelain suction funnel over hard f:Llter and washed twice with 500 ml of diisopropyl ether. Thereafter, the residue is suspended in 600 ml of acetonitrile and digested at room temperature with stirring. Subsequently, the product is filtrated on a porcelain suction funnel, rewashed with 300 ml of acetonitrile and dried to constant weight in a vacuum chamber at 40° C. Subsequently, the crude product Fmoc-ANP(109–126) thus obtained in an amount of 32.3 g is converted to the unprotected ANP (109–126) by addition of diethylamine. The yield is 30.2 g.

Example 10

Condensation of Fragments ANP(109–120) with ANP(121–125) to ANP(109–125)

Following the general procedure described in Example 8, 18.6 g of Fmoc-ANP(109–120) is dissolved in 600 ml of N-methylpyrrolidone. Subsequently, 3.0 g of TBTU (2-(1H-benzotriazol -1-yl)-1,1,3,3-tetramethyluronium tetrafluoroborate), 1.2 g of 1-hydroxybenzotriazole and 3.0 ml of diisopropylethylamine are added to the solution at room temperature with stirring. Thereafter, a solution of H-ANP(121–125)-OtBu, dissolved in 150 ml of N-methylpyrrolidone, is added. In the following, the reaction is monitored by thin layer chromatography. After about 2 hours, the reaction is complete. Then, the reaction mixture is dripped onto 4 l of diisopropyl ether with stirring and subsequently stirred for about 30 minutes. The precipitate is filtrated on a porcelain suction funnel over hard filter and washed twice with 450 ml of diisopropyl ether. Thereafter, the residue is suspended in 500 ml of acetonitrile and digested at room temperature with stirring. Subsequently, the product is filtrated off on a porcelain suction funnel, rewashed with 250 ml of acetonitrile and dried to constant weight in a vacuum chamber at 40° C. Subsequently, the crude product Fmoc-ANP(109–125) thus obtained in an amount of 29.1 g is converted to the unprotected ANP (109–125) by addition of diethylamine. The yield is 28.2 g.

Example 11

Condensation of the Partial Fragments to the Final Product

The intermediate ANP(109–121)-$R^2$ is converted to the final product $R^1$-ANP(105–121)-$R^2$ by condensation with the amino-terminal fragment $R^1$-ANP(105–108) according to the following general process:

The fragment $R^1$-ANP(105–108), the amino terminus of which is protected by an appropriate protecting group, is dissolved in N-methylpyrrolidone. Subsequently, TBTU (2-(1H-benzotriazol-1-yl)-1,1,3,3-tetramethyluronium tetrafluoroborate), 1-hydroxybenzotriazole and diisopropylethylamine are added to the solution at room temperature with stirring. Thereafter, the fragment ANP(109–121)-$R^2$ provided with an appropriate protecting group at the C-terminal end and dissolved in N-methylpyrrolidone is added to the solution. In the following, the reaction is monitored by thin layer chromatography. After about 2 hours, the reaction is complete. Then, the reaction mixture is dripped onto duisopropyl ether with stirring and subsequently stirred for about 30 minutes. The precipitate is filtrated on a porcelain suction funnel over hard filter and washed twice with diisopropyl ether. Thereafter, the residue is suspended in acetonitrile and digested at room temperature with stirring. Subsequently, the product is filtrated off on a porcelain suction funnel, rewashed with acetonitrile and dried to constant weight in a vacuum chamber at 40° C. The thus obtained crude product represents the cardiodilatin fragment $R^1$-ANP(105–121)-$R^2$ protected by appropriate protecting groups at the amino terminus and the C-terminus. Thereafter, the protecting group is removed according to known procedures to obtain the intermediate product H-$R^1$-ANP(109 –121)-$R^2$. Following complete removal of the protecting groups, the obtained cardiodilatin fragment is converted to the cyclized derivative by oxidation and according to known procedures, for example, using iodine.

Example 12

Condensation of Fragments ANP(109–126) and ANP(95–108) to ANP(95–126)

a) Preparation of ANP(95–126)

Following the general procedure described in Example 11, 20.6 g of Boc-ANP(95–108) is dissolved in 400 ml of N-methylpyrrolidone. Subsequently, 2.7 g of TBTU (2-(1Hbenzotriazol-1-yl)-1,1,3,3-tetramethyluronium tetrafluoroborate), 1.3 g of 1-hydroxybenzotriazole and 2.7 ml of diisopropylethylamine are added to the solution at room temperature with stirring. Thereafter, a solution of 29.4 g of H-ANP(109–126)-OtBu, dissolved in 400 ml of N-methylpyrrolidone, is added. In the following, the reaction is monitored by thin layer chromatography. After about 2 hours, the reaction is complete. Then, the reaction mixture is dripped onto 6.5 l of diisopropyl ether with stirring and subsequently stirred for about 30 minutes. The precipitate is filtrated on a porcelain suction funnel over hard filter and washed twice with 500 ml of diisopropyl ether. Thereafter, the residue is suspended in 600 ml of acetonitrile and digested at room temperature with stirring. Subsequently, the product is filtrated off on a porcelain suction funnel, rewashed with 500 ml of acetonitrile and dried to constant weight in a vacuum chamber at 40° C. Subsequently, the crude product Boc-ANP(95–126)-OtBu thus obtained in an amount of 42.5 g is converted to the unprotected ANP (95–126) and dried. The yield is 27.5 g.

b) Cyclization of the deprotected linear ANP(95–126)

60 g of unprotected ANP(95–126) is dissolved in 16 l of 5% acetic acid in deionized water (v/v) and oxidized by addition of 570 ml of a 0.02M methanolic iodine solution. The reaction is complete after 5 minutes. Excess iodine is destroyed by addition of a 0.1M sodium thiosulfate solution. The cyclization solution obtained is subjected directly to further processing.

Example 13

Condensation of Fragments ANP(109–126) and ANP(99–108) to ANP(99–126)

Analogous to the procedure described in Example 12, 22.5 g of Boc-ANP(99–108) is dissolved in 400 ml of N-methylpyrrolidone. Subsequently, 2.9 g of TBTU (2-(1H-benzotriazol-1-yl)-1,1,3,3-tetramethyluronium tetrafluoroborate), 1.4 g of 1-hydroxybenzotriazole and 2.8 ml of diisopropylethylamine are added to the solution at room temperature with stirring. Thereafter, a solution of 30.6 g of H-ANP(109–126)-OtBu, dissolved in 400 ml of N-methylpyrrolidone, is added. In the following, the reaction is monitored by thin layer chromatography. After about 2 hours, the reaction is complete. Then, the reaction mixture is dripped onto 6.5 l of diisopropyl ether with stirring and subsequently stirred for about 30 minutes. The precipitate is filtrated on a porcelain suction funnel over hard filter and washed twice with 500 ml of diisopropyl ether. Thereafter, the residue is suspended in 600 ml of acetonitrile and digested at room temperature with stirring. Subsequently, the product is filtrated off on a porcelain suction funnel, rewashed with 500 ml of acetonitrile and dried to constant weight in a vacuum chamber at 40° C. Subsequently, the crude product Boc-ANP(99–126)-OtBu thus obtained in an amount of 44.7 g is converted to the unprotected ANP (99–126) and dried. The yield is 28.1 g.

Example 14

Condensation of Fragments ANP(109–126) and ANP(102–108) to ANP (102–126)

Analogous to the procedure described in Example 12, 20.4 g of Boc-ANP(102–108) is dissolved in 360 ml of N-methylpyrrolidone. Subsequently, 2.7 g of TBTU (2-(1Hbenzotriazol-1-yl)-1,1,3,3-tetramethyluronium tetrafluoroborate), 1.4 g of 1-hydroxybenzotriazole and 2.6 ml of diisopropylethylamine are added to the solution at room temperature with stirring. Thereafter, a solution of 30.1 g of H-ANP(109–126)-OtBu, dissolved in 400 ml of N-methylpyrrolidone, is added. In the following, the reaction is monitored by thin layer chromatography. After about 2 hours, the reaction is complete. Then, the reaction mixture is dripped onto 6.5 l of diisopropyl ether with stirring and subsequently stirred for about 30 minutes. The precipitate is filtrated on a porcelain suction funnel over hard filter and washed twice with 500 ml of diisopropyl ether. Thereafter, the residue is suspended in 600 ml of acetonitrile and digested at room temperature with stirring. Subsequently, the product is filtrated off on a porcelain suction funnel, rewashed with 500 ml of acetonitrile and dried to constant weight in a vacuum chamber at 40° C. Subsequently, the crude product Boc-ANP(102–126)-OtBu thus obtained in an amount of 41.2 g is converted to the unprotected ANP (102–126) and dried. The yield is 26.9 g.

Example 15

Purification of ANP(95–126) and Preparation of the High-Purity Form a) Concentrating the cyclized urodilatin [ANP(95–126)]

The cyclization solution (about 17 liters of 5% AcOH, in deionized water (v/v), contains about 60 g of cyclized urodilatin) is applied (flow rate 130 ml/min) on a glass column (diameter: 70 mm, length: 900 mm, filled with Vydac 218 TPB 2030) equilibrated with 1000 ml of buffer A3 (0.1% TFA (v/v) in deionized water).

Once application by pumping is finished, the peptide is eluted by continuous charging of buffer B3 (0.1% TFA in deionized water/ACN 2:3 v/v) in a continuous gradient (0% buffer B during 40 min; 15–35% buffer B during 90 min; 35% buffer B during 10 min; flow rate 130 ml/min).

urodilatin fractions showing a purity of more than 75% on monitoring by analytical HPLC are combined. These combined fractions are diluted with one volume equivalent of deionized water and applied (flow rate 140 ml/min) on a Biotage module (diameter: 75 mm, length: 300 mm, filled with YMC $C_{18}$, 120 A, 10 μm) equilibrated with 300 ml of buffer A3.

Subsequently, the concentrated peptide is eluted by washing the column with 100% buffer B3, and the acetonitrile is evaporated. The remaining solution is lyophilized.

Between 17 and 20 g of urodilatin with a purity of more than 90% is obtained.

b) Purification of the concentrated urodilatin 4.5 g of the concentrated urodilatin is dissolved in 250 ml of 10% AcOH in deionized water (v/v) and applied (flow rate 140 ml/min) on a Biotage module (diameter: 75 mm, length: 300 mm, filled with YMC $C_{18}$, 120 A, 10 μm) equilibrated with 300 ml of buffer A4 (50 mM TEAP, pH 2.25, in deionized water).

The peptide is eluted by continuous charging of buffer B4 (50 mM TEAP, pH 2.25 in deionized water/ACN 2:3 v/v) in a continuous gradient (22–28% B during 90 min; 28% B during 10 min; 28–40% B during 20 min; flow rate 140 ml/min).

urodilatin fractions showing a purity of more than 99% and impurities of not more than 0.5% on monitoring by analytical HPLC are combined. These combined fractions are diluted with one volume equivalent of deionized water and pumped onto the Biotage module previously cleaned with 1000 ml of buffer B3 and subsequently equilibrated with 300 ml of buffer A3. For desalting, a washing with 1200 ml of buffer A3 is made The pure product is eluted by washing the column with 1500 ml of buffer B3, and the acetonitrile is evaporated. The remaining solution is lyophilized.

The result is between 2.3 and 2.7 g of high-purity urodilatin.

c) Resalting of urodilatin×TFA to urodilatin acetate 2.5 g of high-purity urodilatin x TFA salt is dissolved in 80 ml of 5% AcOH, in deionized water v/v, and applied to a chromatography column (diameter: 20 mm, length: 300 mm, filled with 40 ml of Merck ion exchanger III acetate form) washed with 5% AcOH. A washing with 40 ml of 5% AcOH is made. The eluate, about 125 ml, is applied once more to the same ion exchange column. A washing with 55 ml of 5% AcOH is made. The eluate, about 180 ml, is filtrated clear over a polysulfone membrane (diameter 47 mm, 0.2 μm). The solution is lyophilized.

The result is between 2.05 and 2.30 g of high-purity urodilatin acetate.

Example 16

Purification of ANP(99–126) and Preparation of the High-Purity Form a) Concentrating the cyclized cardiodilatin fragment ANP (99–126)

Analogous to Example 15a), the cyclization solution (about 15 liters of 5% AcOH, in deionized water (v/v), with a peptide content of about 50 g) is applied (flow rate 130 ml/min) on a glass column equilibrated with 1000 ml of buffer A3 (0.1% TFA (v/v) in deionized water). Once application by pumping is finished, the peptide is eluted by continuous charging of buffer B3 (0.1% TFA in deionized water/ACN 2:3 v/v) in a continuous gradient (0% buffer B during 40 min; 15–35% buffer B during 90 min; 35% buffer B during 10 min;

flow rate 130 ml/min). Peptide fractions showing a purity of more than 75% on monitoring by analytical HPLC are combined. These combined fractions are diluted with one volume equivalent of deionized water and applied (flow rate 140 ml/min) on a Biotage module equilibrated with 300 ml of buffer A3. Subsequently, the concentrated peptide is eluted by washing the column with 100% buffer B3, and the acetonitrile is evaporated. The remaining solution is lyophilized.

The result is between 14 and 17 g of cardiodilatin fragment ANP(99–126) with a purity of more than 90%.

b) Purification of the concentrated ANP(99–126)

3.5 g of the cardiodilatin fragment concentrated according to Example 16a) is dissolved in 200 ml of 10% AcOH in deionized water (v/v) and applied (flow rate 140 ml/min) on a Biotage module equilibrated with 300 ml of buffer A4 (50 mM TEAP, pH 2.25, in deionized water). The peptide is eluted by continuous charging of buffer B4 (50 mM TEAP, pH 2.25 in deionized water/ACN 2:3 v/v) in a continuous gradient (22–28% B during 90 min; 28% B during 10 min; 28–40% B during 20 min; flow rate 140 ml/min).

Peptide fractions showing a purity of more than 99% and impurities of not more than 0.5% on monitoring by analytical HPLC are combined. These combined fractions are diluted with one volume equivalent of deionized water and pumped onto the Biotage module previously cleaned with 1000 ml of buffer B3 and subsequently equilibrated with 300 ml of buffer A3. For desalting, a washing with 1000 ml of buffer A3 is made.

The pure product is eluted by washing the column with 1500 ml of buffer B3, and the acetonitrile is evaporated. The remaining solution is lyophilized.

The result is between 1.7 and 2.2 g of high-purity cardiodilatin fragment ANP(99–126). Analogous to the procedure described in Example 14c), this fragment is converted to the corresponding acetate salt. The result is between 1.3 and 1.7 g of high-purity ANP(99–126) acetate.

Example 17

Purification of ANP(102–126) and Preparation of the HilhPurity Form a) Concentrating the cyclized cardiodilatin fragmeant ANP (102–126)

Analogous to Example 15a), the cyclization solution (about 18 liters of 5% AcOH, in deionized water (v/v), with a peptide content of about 65 g) is applied (flow rate 130 ml/min) on a glass column equilibrated with 1000 ml of buffer A3 (0.1% TFA (v/v) in deionized water) . Once application by pumping is finished, the peptide is eluted by continuous charging of buffer B3 (0.1% TFA in deionized water/ACN 2:3 v/v) in a continuous gradient (0% buffer B during 40 min; 15–35% buffer B during 90 min; 35% buffer B during 10 min; flow rate 130 ml/min) . Peptide fractions showing a purity of more than 75% on monitoring by analytical HPLC are combined. These combined fractions are diluted with one volume equivalent of deionized water and applied (flow rate 140 ml/min) on a Biotage module equilibrated with 300 ml of buffer A3. Subsequently, the concentrated peptide is eluted by washing the column with 100% buffer B3, and the acetonitrile is evaporated. The remaining solution is lyophilized.

The result is between 19 and 23 g of cardiodilatin fragment ANP(102–126) with a purity of more than 90%.

b) Purification of the concentrated ANP(102–126)

4.8 g of the cardiodilatin fragment concientrated according to Example 17a) is dissolved in 200 ml of 10% AcOH in deionized water (v/v) and applied (flow rate 140 ml/min) on a Biotage module equilibrated with 300 ml of buffer A4 (50 mM TEAP, pH 2.25, in deionized water). The peptide is eluted by continuous charging of buffer B4 (50 mM TEAP, pH 2.25 in deionized water/ACN 2:3 v/v) in a continuous gradient (22–28% B during 90 min; 28% B during 10 min; 28–40% B during 20 min; flow rate 140 ml/min).

Peptide fractions showing a purity of more than 99% and impurities of not more than 0.5% on monitoring by analytical HPLC are combined. These combined fractions are diluted with one volume equivalent of deionized water and pumped onto the Biotage module previously cleaned with 1000 ml of buffer B3 and subsequently equilibrated with 300 ml of buffer A3. For desalting, a washing with 1000 ml of buffer A3 is made.

The pure product is eluted by washing the column with 1500 ml of buffer B3, and the acetonitrile is evaporated. The remaining solution is lyophilized.

The result is between 1.9 and 2.4 g of high-purity cardiodilatin fragment ANP(102–126) . Analogous to the procedure described in Example 14c), this fragment is converted to the corresponding acetate salt. The result is between 1.5 and 1.9 g of high-purity ANP(99–126) acetate.

Example 18

Analytical HPLC Examinations Using the ANP (95–126) Example a) Elution with TEAP buffer, pH 2.25

50 μg of ANP(95–126) is injected onto an analytical HPLC column. A linear gradient of buffer B of 25–45% during 20 minutes (buffer A: 50 mM TEAP, pH 2.25; buffer B: mixture of A and acetonitrile at: a volume ratio of 2:3) served as the eluant. The chromatogram in FIG. 5 reveals that two polar impurities are contained which may be separated by the eluant employed.

Legend to FIG. 5:
25–45% in 20 min.
Buffer A: 50mM TEAP pH 2.25
Buffer B: A:ACN (2:3)
215 nm 1.0 ml/'C-Nr. 4040465 C
M+N 250/1/4°/3 Nuc 300 A5 u C18
D-2500
Method: 50 μg; TAG 243 CH:1; Peak reject: 5000
File: 1; Calculation method: area%; Table: 0; conc: area

| No. | RT | Area | % | BC |
|---|---|---|---|---|
| 5 | 7,82 | 53358 | 0,311 | BV |
| 6 | 8,08 | 84196 | 0,491 | VV |
| 7 | 9,07 | 386602 | 2,255 | VV |
| 8 | 9,78 | 1265799 | 7,384 | VV |
| 9 | 10,56 | 4701290 | 27,430 | VV |
| 10 | 10,92 | 10557085 | 61,582 | VV |
| 11 | 11,91 | 27613 | 0,161 | TBB |
| 12 | 12,82 | 8763 | 0,051 | TBB |
| 13 | 13,76 | 14346 | 0,084 | BB |
| 14 | 14,86 | 31959 | 0,186 | BB |
| 15 | 19,04 | 10892 | 0,064 | BB |
| Total | | 17143003 | 100,00 | | b) Elution with 0.1% TFA (trifluoroacetic acid)

Analogous to Example 18a), 50 μg of ANP(95–26) same production batch is applied onto an analytical HPLC column. A linear gradient of buffer B of 30–50% during 20 minutes (buffer A: 0.1% TFA in water; buffer B: mixture of A and acetonitrile at a volume ratio of 2:3) served as the eluant. The chromatogram in FIG. 6 reveals that separation of the contained impurities by means of this eluant is not effected. Compared to the chromatogram in Example a), the main peak is broader and the isolated product contains both of the polar purities which can be recognized in the chromatogram of FIG. 5.

Legend to FIG. 6:
30–50% B in 20 min.
Buffer A: 0.1% TFA in water
Buffer B: A:AND(2:3)
215 nm 1.0 ml/'C-Nr. 4011079 C
M+N 250/1/4°/3 Nuc 300 LA 5u C18
D-2500
Method: 50 μg; TAG 142; CH:1; Peak reject: 5000
FIle: 2; Calculation method; area%. Table: 0; conc: area

| No. | RT | Area | % | BC |
|---|---|---|---|---|
| 2 | 3,64 | 5073 | 0,040 | BV |
| 4 | 5,10 | 6624 | 0,053 | BB |
| 5 | 5,92 | 8161 | 0,065 | BB |
| 6 | 7,36 | 6814 | 0,054 | BB |
| 7 | 9,11 | 252878 | 2,012 | BB |
| 9 | 11,73 | 87629 | 0,697 | BB |
| 10 | 12,60 | 258273 | 2,055 | BB |
| 11 | 13,09 | 4578590 | 36,428 | VV |
| 12 | 13,26 | 7175177 | 57,086 | VV |
| 13 | 14,67 | 179155 | 1,425 | TBB |
| 14 | 17,48 | 10611 | 0,084 | BB |
| Total | | 12568985 | 100,00 | |

EXAMPLE 19

Purity Check by Capillary Electrophoresis

Lyophilized samples of the final products of cardiodilatin fragments from Examples 15 through 17 are dissolved in water at a concentration of 1 mg/ml and analyzed immediately. Capillary electrophoresis was performed using the Beckmann P/ACE 2100 system under the following conditions:

Capillary: Fused Silica by Supelco, separation length 50 cm, internal diameter 75 μm Detection wave length: 200 nm Injection period: 1 s Separation buffer: 100 mM sodium phosphate, pH 2.5; 0.02% hydroxypropylmethylcellulose Separation parameters: 25° C., 80 μm, 30 min FIG. 3 shows the chromatogram obtained for prior art urodilatin.

FIG. 4 shows the chromatogram for high-purity urodilatin obtained according to Example 15.

A comparison of both chromatograms reveals that the urodilatin according to the invention differs significantly from prior art urodilatin. The urodilatin according to the invention is free of peptide impurities.

INDEX OF ABBREVIATIONS

| Amino acids | |
|---|---|
| Ala | L-Alanine |
| Asn | L-Asparagine |
| Asp | L-Asparaginic acid |
| Arg | L-Arginine |
| Cys | L-Cysteine |
| Gln | L-Glutamine |
| Gly | Glycine |
| Ile | L-Isoleucine |
| Leu | L-Leucine |
| Met | L-Methionine |
| Phe | L-Phenylalanine |
| Pro | L-Proline |
| Ser | L-Serine |
| Thr | L-Threonine |
| Tyr | L-Tyrosine |
| Protecting groups | |
| Boc | t-Butyloxycarbonyl |
| Fmoc | 9-Fluorenylmethoxycarbonyl |
| OtBu | t-Butyl ester |
| Pbf | 2,2,4,6,7-Pentamethyldihydrobenzofuran-5-sulfonyl |
| Pmc | 2,2,5,7,8-Pentamethylchroman-6-sulfonyl |
| tBu | t-Butyl ether |
| Acm | Acetamidomethyl |
| Trt | Trityl |
| Reagents/Solvents | |
| ACN | Acetonitrile |
| TFA | Trifluoroacetic acid |
| TEAP | Triethylammonium phosphate |

We claim:

1. A process for the preparation of a lineaer or cyclic cardiodilatin fragment having the formula $$R^1\text{—ANP (105-121)—}R^2$$

wherein said cardiodilatin fragment has a total chain length of 17-37 amino acids, wherein ANP (105-121) is the amino acid sequence according to SEQ ID NO. 1, R' is absent or an amino acid chain of sequence ANP (90-104) (SEQ ID NO. 2) or a fragment thereof, and $R^2$ is absent or an amino acid chain of sequence ANP (122-126) (SEQ ID NO. 3) or a fragment thereof, comprising condensing at least three partial fragments to form said cardiolilation fragment, wherein a first condensation of said partial fragments is carried out between amino acid positions $Gly^{108}$ and $Arg^{109}$ and a second condensation is carried out between amino acid positions $Gly^{120}$ and $Cys^{121}$ and wherein one of said partial fragments is ANP (109-120).

2. The process according to claim 1, wherein condensation of the partial fragments is (a) first effected between the amino acid positions $Gly^{120}$ and $Cys^{121}$ using the partial fragments ANP (109-120) and $Cys^{121}$—$R^2$, and (b) then condensation of the partial fragments is effected between the amino acid positions $Gly^{108}$ and $Arg^{109}$ using the partial fragment ANP (109-120)—$R^2$ obtained in step (a), and the partial fragment $R^1$—ANP (105-108).

3. The process according to claim 1, wherein $R^2$ is the amino acid sequence ANP(122-126) (SEQ ID NO:3), further comprising synthesizing a fragment Fmoc-ANP(109–120)—OH on a solid support phase according to the Merrifield process and subsequently removing said fragment Fmoc-ANP (109–120)—OH from said solid phase, condensing said fragment Fmoc-ANP(109–120)—OH with a fragment H-ANP(121–126)—OtBu to produce a fragment Fmoc-AND(109–126) —OtBu and subsequently removing the Fmoc protecting group from the resulting fragment Fmoc-ANP(109–126) —OtBu.

4. The process according to claim 1, wherein R' represents the amino acid fragment ANP(95–104), further comprising synthesizing a fragment Boc-ANP(95–108)—OH, on a solid support phase using the Merrifield process, removing the fragment Boc-ANP(95–108) —OH from said solid support, condensing said fragment BocANP(95–108) —OH with a fragment H-ANP(109–126) -OtBu to produce a fragment Boc-ANP(95–126)—OtBu, and subsequently removing the Boc and OtBu protecting groups from the fragment Boc-ANP(95–126)—OtBu.

5. The process according to claim 1, wherein the three partial fragments $R^1$-ANP(105–108), ANP(109–120) or ANP(121)—$R^2$ are produced on a solid support material according to the Merrifield process, and said fragments are bound to said solid support material by a super acid-sensitive linker.

6. The process according to claim 1, wherein the cardiodilatin fragment $R^1$ANP(105–121)—$R^2$ is fully protected, further comprising removing the amino and hydroxy protecting groups from the fully protected cardiodilatin fragment $R^1$-ANP (105–121)—$R^2$ to form a fragment protected by the protecting group Acm at $Cys^{105}$, subsequently removing the protecting group Acm from the fragment protected by the protecting group Acm, and thereafter cyclizing the cardiodilatin fragment by oxidation.

7. The process according to claim 1, wherein the $R^1$ is a fragment select(ed from the group consisting of ANP (95–104), ANP(99–104) and ANP(102–104).

8. The process according to claim 1, wherein $R^2$ is a fragment selected from the group consisting of ANP (122–125) and ANP (122–126).

* * * * *